United States Patent [19]

Conneely et al.

[11] Patent Number: 5,571,896
[45] Date of Patent: *Nov. 5, 1996

[54] PRODUCTION OF RECOMBINANT HUMAN LACTOFERRIN

[75] Inventors: Orla M. Conneely, Houston, Tex.; Denis R. Headon, Galway, Ireland; Bert W. O'Malley; Gregory S. May, both of Houston, Tex.

[73] Assignee: Baylor College of Medicine, Houston, Tex.

[*] Notice: The term of this patent shall not extend beyond the expiration date of Pat. No. 5,571,691.

[21] Appl. No.: 250,308

[22] Filed: May 27, 1994

Related U.S. Application Data

[63] Continuation of Ser. No. 873,304, Apr. 24, 1992, abandoned.
[51] Int. Cl.$^6$ .......................... C07K 14/79; C12N 15/12; C12N 15/62; C12N 15/80
[52] U.S. Cl. .......................... 530/400; 530/395; 530/412; 435/69.1; 435/69.7; 435/259.11; 435/254.2; 435/254.21; 435/254.23; 435/254.3; 435/320.1; 536/23.4; 536/23.5; 536/24.1; 935/10; 935/27; 935/28; 935/37; 935/48; 935/68; 935/69
[58] Field of Search .......................... 536/23.5, 23.4, 536/23.74; 435/254, 254.11, 320.1, 69.1, 254.21, 254.23, 254.3, 254.22, 254.2, 69.7; 530/394, 395, 350

[56] References Cited

U.S. PATENT DOCUMENTS

| 4,652,639 | 3/1987 | Stabinsky | 435/91.52 |
|---|---|---|---|
| 4,740,461 | 4/1988 | Kaufman | 435/69.1 |
| 5,155,037 | 10/1992 | Summers | 435/240.2 |
| 5,304,633 | 4/1994 | Tomita et al. | 530/326 |

FOREIGN PATENT DOCUMENTS

| PCT/US87/00119 | 1/1987 | WIPO. | |
|---|---|---|---|
| PCT/DK88/00245 | 9/1988 | WIPO. | |
| WO91/13982 | 9/1991 | WIPO | 530/400 |

OTHER PUBLICATIONS

Epstein, J. B., et al., Reviews of Infectious Diseases, vol. 6, No. 1, "Oral Candidiasis: Pathogenesis and Host Defense", pp. 96–106. 1984.

Soukka, T., et al., FEMS Microbiology Letters, vol. 90, "Fungicidal effect of human lactoferrin against *Candida albicans*", pp. 223–228 (1992).

M. Metz–Boutigue et al. "Human lactotransferrin: amino sequence and structural comparisons with other transferrins" *Eur. J. Bioch.*, 145:659–676 (1984).

B. Anderson et al.; "Structure of Human Lactoferrin: Crystallographic Structure Analysis and Refinement at 1–8 A Resolution" *J. Mol. Biol.* 209:711–734 (1989).

K. Stowell et al.; "Expression of cloned human lactoferrin in baby–hamster kidney cells" *Biochem. J.*, 276:349–355 (1991).

P. Mead et al.; "cDNA and protein sequence of bovine lactoferrin" *Nucleic Acids Research*, 18:7167, No. 18 (1990).

M. Rey et al.; "Complete nucleotide sequence of human mammary gland lactoferrin", 18:5288, No. 17 (1990).

M. Powell et al.; "Nucleotide sequence of human lactoferrin cDNA" *Nucleic Acids Research*, 18:4013, No. 13 (1990).

(List continued on next page.)

*Primary Examiner*—Robert A. Wax
*Assistant Examiner*—William W. Moore
*Attorney, Agent, or Firm*—Albert P. Halluin; Pennie & Edmonds

[57] ABSTRACT

The present invention provides novel plasmids, transfected eucaryotic cells and methods of producing these plasmids and transfected eucaryotic cells. The novel plasmid contains the cDNA for human lactoferrin protein. Methods for the production of human lactoferrin protein in *A. Oryzae* are also provided. Thus, the present invention provides an efficient and economical means for the production of recombinant human lactoferrin protein.

24 Claims, 10 Drawing Sheets

OTHER PUBLICATIONS

B. Pentecost et al.; "Lactotransferrin Is the Major Estrogen Inducible Protein of Mouse Uterine Secretions" *J. Biological Chem.*, 262:10134–10139, No. 21 (1987).

T. Rado et al.; "Isolation of Lactoferrin cDNA From a Human Myeloid Library and Expressions of mRNA During Normal and Leukemic Myelopoiesis" *Blood*, 70:989–993, No. 4 (1987).

A. Pierce et al.; "Molecular cloning and sequence analysis of bovine lactotransferrin" *Eur. J. Biochem.*, 196:177–184 (1991).

Valenti et al. 1986, FEMS Microbiology Letters 33:271–275.

Promego, 1988/89, Price List, 2800 S. Fish Hatchery Road, Madison, WI.

Huge–Jensen et al. 1989. Lipids, 24(9): 781–785.

Siner et al. 1989. Gene, 79:107–117.

von Heyne, G. 1984, J. Mol. Biol. 173:243–251.

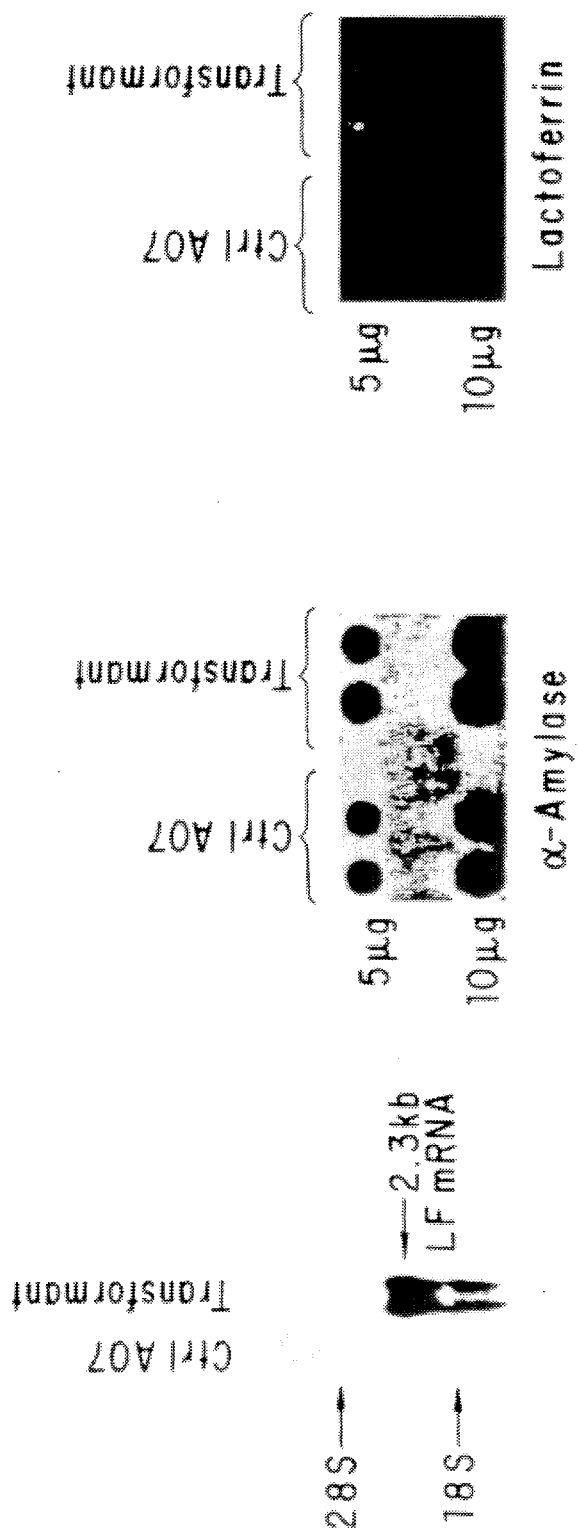

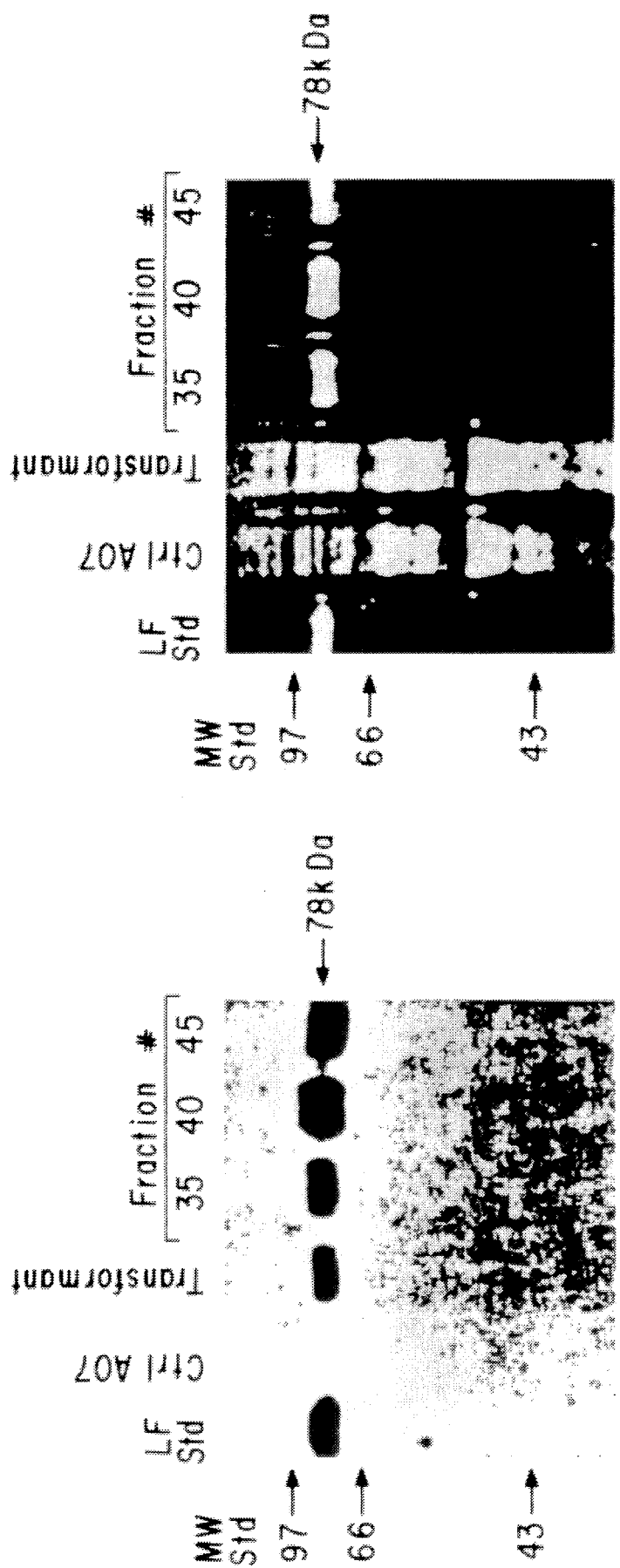

```
                                         Mature α-Amylase
     α-Amlase Signal Sequence       ┌
1) ─────────────────── AlaLeuAlaAlaThrProAlaAspTrpArgSerGlnSer Mature Human Lactoferrin
    Lactoferrin Signal Sequence  ┌
2) ─────────────────── CysLeuAlaGlyArgArgArgArgSerValGlnTrpCys Mature Recombinant Lactoferrin
     α-Amylase Signal Sequence      ┌
3) ─────────────────── AlaLeuAlaAlaGlyArgArgArgArgSerValGlnTrp
```

FIG. 4C

```
                                                            1
                                                    GAATTCC GACCGCAGAC
   18
   ATG AAA CTT GTC TTC CTC GTC CTG CTG TTC CTC GGG GCC CTC GGA CTG
   met lys leu val phe leu val leu leu phe leu gly ala leu gly leu
     1
   66
   TGT CTG GCT GGC CGT AGG AGA AGG AGT GTT CAG TGG TGC ACC GTA TCC
   cys leu ala gly arg arg arg arg ser val gln trp cys thr val ser
    17
  114
   CAA CCC GAG GCC ACA AAA TGC TTC CAA TGG CAA AGG AAT ATG AGA AGA
   gln pro glu ala thr lys cys phe gln trp gln arg asn met arg arg
    33
  162
   GTG CGT GGC CCT CCT GTC AGC TGC ATA AAG AGA GAC TCC CCC ATC CAG
   val arg gly pro pro val ser cys ile lys arg asp ser pro ile gln
    49
  210
   TGT ATC CAG GCC ATT GCG GAA AAC AGG GCC GAT GCT GTG ACC CTT GAT
   cys ile gln ala ile ala glu asn arg ala asp ala val thr leu asp
    65
  258
   GGT GGT TTC ATA TAC GAG GCA GGC CTG GCC CCC TAC AAA CTG CGA CCT
   gly gly phe ile tyr glu ala gly leu ala pro tyr lys leu arg pro
    81
  306
   GTA GCG GCG GAA GTC TAC GGG ACC GAA AGA CAG CCA CGA ACT CAC TAT
   val ala ala glu val tyr gly thr glu arg gln pro arg thr his tyr
    97
  354
   TAT GCC GTG GCT GTG GTG AAG AAG GGC GGC AGC TTT CAG CTG AAC GAA
   tyr ala val ala val val lys lys gly gly ser phe gln leu asn glu
   113
  402
   CTG CAA GGT CTG AAG TCC TGC CAC ACA GGC CTT CGC AGG ACC GCT GGA
   leu gln gly leu lys ser cys his thr gly leu arg arg thr ala gly
   129
  450
   TGG AAT GTG CCT ATA GGG ACA CTT CGT CCA TTC TTG AAT TGG ACG GGT
   trp asn val pro ile gly thr leu arg pro phe leu asn trp thr gly
   145
```

FIG. 6A

```
498
CCA CCT GAG CCC ATT GAG GCA GCT GTG GCC AGG TTC TTC TCA GCC AGC
pro pro glu pro ile glu ala ala val ala arg phe phe ser ala ser
161
546
TGT GTT CCC GGT GCA GAT AAA GGA CAG TTC CCC AAC CTG TGT CGC CTG
cys val pro gly ala asp lys gly gln phe pro asn leu cys arg leu
177
594
TGT GCG GGG ACA GGG GAA AAC AAA TGT GCC TTC TCC TCC CAG GAA CCG
cys ala gly thr gly glu asn lys cys ala phe ser ser gln glu pro
193
642
TAC TTC AGC TAC TCT GGT GCC TTC AAG TGT CTG AGA GAC GGG GCT GGA
tyr phe ser tyr ser gly ala phe lys cys leu arg asp gly ala gly
209
690
GAC GTG GCT TTT ATC AGA GAG AGC ACA GTG TTT GAG GAC CTG TCA GAC
asp val ala phe ile arg glu ser thr val phe glu asp leu ser asp
225
738
GAG GCT GAA AGG GAC GAG TAT GAG TTA CTC TGC CCA GAC AAC ACT CGG
glu ala glu arg asp glu tyr glu leu leu cys pro asp asn thr arg
241
786
AAG CCA GTG GAC AAG TTC AAA GAC TGC CAT CTG GCC CGG GTC CCT TCT
lys pro val asp lys phe lys asp cys his leu ala arg val pro ser
257
834
CAT GCC GTT GTG GCA CGA AGT GTG AAT GGC AAG GAG GAT GCC ATC TGG
his ala val val ala arg ser val asn gly lys glu asp ala ile trp
273
882
AAT CTT CTC CGC CAG GCA CAG GAA AAG TTT GGA AAG GAC AAG TCA CCG
asn leu leu arg gln ala gln glu lys phe gly lys asp lys ser pro
289
930
AAA TTC CAG CTC TTT GGC TCC CCT AGT GGG CAG AAA GAT CTG CTG TTC
lys phe gln leu phe gly ser pro ser gly gln lys asp leu leu phe
305
978
AAG GAC TCT GCC ATT GGG TTT TCG AGG GTG CCC CCG AGG ATA GAT TCT
lys asp ser ala ile gly phe ser arg val pro pro arg ile asp ser
321
1026
GGG CTG TAC CTT GGC TCC GGC TAC TTC ACT GCC ATC CAG AAC TTG AGG
gly leu tyr leu gly ser gly tyr phe thr ala ile gln asn leu arg
337
```

FIG. 6B

1074
AAA AGT GAG GAG GAA GTG GCT GCC CGG CGT GCG CGG GTC GTG TGG TGT
lys ser glu glu glu val ala ala arg arg ala arg val val trp cys
353

1122
GCG GTG GGC GAG CAG GAG CTG CGC AAG TGT AAC CAG TGG AGT GGC TTG
ala val gly glu gln glu leu arg lys cys asn gln trp ser gly leu
369

1170
AGC GAA GGC AGC GTG ACC TGC TCC TCG GCC TCC ACC ACA GAG GAC TGC
ser glu gly ser val thr cys ser ser ala ser thr thr glu asp cys
385

1218
ATC GCC CTG GTG CTG AAA GGA GAA GCT GAT GCC ATG AGT TTG GAT GGA
ile ala leu val leu lys gly glu ala asp ala met ser leu asp gly
401

1266
GGA TAT GTG TAC ACT GCA GGC AAA TGT GGT TTG GTG CCT GTC CTG GCA
gly tyr val tyr thr ala gly lys cys gly leu val pro val leu ala
417

1314
GAG AAC TAC AAA TCC CAA CAA AGC AGT GAC CCT GAT CCT AAC TGT GTG
glu asn tyr lys ser gln gln ser ser asp pro asp pro asn cys val
433

1362
GAT AGA CCT GTG GAA GGA TAT CTT GCT GTG GCG GTG GTT AGG AGA TCA
asp arg pro val glu gly tyr leu ala val ala val val arg arg ser
449

1410
GAC ACT AGC CTT ACC TGG AAC TCT GTG AAA GGC AAG AAG TCC TGC CAC
asp thr ser leu thr trp asn ser val lys gly lys lys ser cys his
465

1458
ACC GCC GTG GAC AGG ACT GCA GGC TGG AAT ATC CCC ATG GGC CTG CTC
thr ala val asp arg thr ala gly trp asn ile pro met gly leu leu
481

1506
TTC AAC CAG ACG GGC TCC TGC AAA TTT GAT GAA TAT TTC AGT CAA AGC
phe asn gln thr gly ser cys lys phe asp glu tyr phe ser gln ser
497

1554
TGT GCC CCT GGG TCT GAC CCG AGA TCT AAT CTC TGT GCT CTG TGT ATT
cys ala pro gly ser asp pro arg ser asn leu cys ala leu cys ile
513

1602
GGC GAC GAG CAG GGT GAG AAT AAG TGC GTG CCC AAC AGC AAT GAG AGA
gly asp glu gln gly glu asn lys cys val pro asn ser asn glu arg
529

FIG. 6C

```
1650
    TAC TAC GGC TAC ACT GGG GCT TTC CGG TGC CTG GCT GAG AAT GCT GGA
    tyr tyr gly tyr thr gly ala phe arg cys leu ala glu asn ala gly
    545
1698
    GAC GTT GCA TTT GTG AAA GAT GTC ACT GTC TTG CAG AAC ACT GAT GGA
    asp val ala phe val lys asp val thr val leu gln asn thr asp gly
    561
1746
    AAT AAC AAT GAG GCA TGG GCT AAG GAT TTG AAG CTG GCA GAC TTT GCG
    asn asn asn glu ala trp ala lys asp leu lys leu ala asp phe ala
    577
1794
    CTG CTG TGC CTC GAT GGC AAA CGG AAG CCT GTG ACT GAG GCT AGA AGC
    leu leu cys leu asp gly lys arg lys pro val thr glu ala arg ser
    593
1842
    TSC CAT CTT GCC ATG GCC CCG AAT CAT GCC GTG GTG TCT CGG ATG GAT
    cys his leu ala met ala pro asn his ala val val ser arg met asp
    609
1890
    AAG GTG GAA CGC CTG AAA CAG GTG CTG CTC CAC CAA CAG GCT AAA TTT
    lys val glu arg leu lys gln val leu leu his gln gln ala lys phe
    625
1938
    GGG AGA AAT GGA TCT GAC TGC CCG GAC AAG TTT TGC TTA TTC CAG TCT
    gly arg asn gly ser asp cys pro asp lys phe cys leu phe gln ser
    641
1986
    GAA ACC AAA AAC CTT CTG TTC AAT GAC AAC ACT GAG TGT CTG GCC AGA
    glu thr lys asn leu leu phe asn asp asn thr glu cys leu ala arg
    657
2034
    CTC CAT GGC AAA ACA ACA TAT GAA AAA TAT TTG GGA CCA CAG TAT GTC
    leu his gly lys thr thr tyr glu lys tyr leu gly pro gln tyr val
    673
2082
    GCA GGC ATT ACT AAT CTG AAA AAG TGC TCA ACC TCC CCC CTC CTG GAA
    ala gly ile thr asn leu lys lys cys ser thr ser pro leu leu glu
    689
2130
    GCC TGT GAA TTC CTC AGG AAG TAA
    ala cys glu phe leu arg lys ***  ACCGAA GAAGATGGCC CAGCTCCCCA
    705
2180
    AGAAAGCCTC AGCCATTCAC TGCCCCAGC TCTTCTCCCC AGGTGTGTTG GGGCCTTGGC

2240
    TCCCCTGCTG AAGGTGGGGA TTGCCCATCC ATCTGCTTAC AATTCCCTGC TGTCGTCTTA

2300
    GCAAGAAGTA AAATGAGAAA TTTTGTTGAA AAAAAAAAAA AAAAAAAAAA AAAAAAAA
```

PRODUCTION OF RECOMBINANT HUMAN LACTOFERRIN

This invention was made with government support under Grant No. HD 27965 awarded by the National Institute of Health. The government has certain rights in the invention.

This is a continuation, of application Ser. No. 07/873,304, filed Apr. 24, 1992, now abandoned.

BACKGROUND OF THE INVENTION

1. Field of the Invention

The present invention relates generally to the field of iron-binding glycoproteins. More specifically, the present invention relates to the recombinant production of human lactoferrin.

2. Description of the Related Art

Human lactoferrin (LF) is a member of the transferrin family of iron-binding monomeric glycoproteins. It was originally discovered in milk where it can reach levels of 7 grams/liter in colostrum. LF has since been detected in other external fluids such as tears, saliva and mucosal secretions and also in the secondary granules of polymorphonuclear leukocytes.

LF is a 78 kDa glycoprotein having a bilobal structure with a high degree of homology between the C and N terminal halves which is evident at both the amino acid and three dimensional structural level. Each of these lobes can reversibly bind one ferric iron with high affinity and with the concomitant binding of bicarbonate. The biological functions proposed for lactoferrin include protection against microbial infection, enhanced intestinal iron absorption in infants, promotion of cell growth, regulation of myelopoiesis and modulation of inflammatory responses.

Filamentous fungi have been successfully employed as hosts in the industrial production of extracellular glycoproteins. Certain industrial strains are capable of secreting gram quantities of these proteins. In addition, filamentous fungi are able to correctly perform post-translational modifications of eucaryotic proteins and many strains have U.S Food and Drug Administration approval. Furthermore, large scale fermentation technology and downstream processing experience is available.

Currently, there is no efficient and economical way to produce human LF. Consequently, a long felt need and description in this art would be met by the development of an efficient method for the production of human lactoferrin for nutritional and therapeutic applications and for further investigation into its mechanism of action.

SUMMARY OF THE INVENTION

In one embodiment, the present invention provides for a recombinant plasmid comprising the cDNA of human lactoferrin. The plasmid of the present invention is adapted for expression in an eucaryotic cell and contains the regulatory elements necessary for the expression of the human lactoferrin cDNA in this eucaryotic cell.

In another embodiment, the present invention provides for a transformed eucaryotic cell which includes a recombinant plasmid. The eucaryotic cell is selected from a group of filamentous fungi comprising Aspergillus. The plasmid contains a plasmid vector into which a polydeoxyribonucleotide segment coding for human lactoferrin protein has been inserted.

2

In yet another embodiment of the present invention, there is provided a process for producing recombinant human lactoferrin which comprises culturing a transformant eucaryotic cell, which includes a recombinant plasmid. The plasmid contains a plasmid vector having a polydeoxyribonucleotide coding for the human lactoferrin protein. After culturing in a suitable nutrient medium until human lactoferrin protein is formed, the human lactoferrin protein is isolated.

In still yet another embodiment of the present invention, there is provided a recombinant expression vector. This vector comprises a transcriptional unit comprising an assembly of (1) a genetic element or elements having a regulatory role in gene expression; (2) cDNA coding for human lactoferrin; (3) appropriate transcription and translation initiation and termination sequences; and (4) a genetic element for selection of aspergillus spores that have been transformed with the vector.

In still yet another embodiment of the present invention, there is provided a method for producing biologically active recombinant lactoferrin. The method comprises synthesizing sequences containing a selectable marker gene, a promotor, a transcription termination sequence, and a linker sequence; cloning the sequences to form a plasmid; digesting the plasmid with a restriction endonuclease; inserting a cDNA coding for lactoferrin into a restriction site; and transforming eucaryotic cells with the plasmid expressing lactoferrin cDNA.

BRIEF DESCRIPTION OF THE DRAWINGS

So that the manner in which the above recited features, advantages, and objects of the invention, as well as others which will become clear, are obtained and can be understood in detail, more particular descriptions of the invention briefly summarized above may be had by reference to certain embodiments thereof which are illustrated in the appended drawings. These drawings form a part of this specification. It is to be noted, however, that the appended drawings illustrate preferred embodiments of the invention and therefore not to be considered limiting of its scope. The invention may admit to other equally effective equivalent embodiments.

FIG. 3 depicts an RNA analysis of transformant versus control A07.

FIG. 4 shows the silver stained SDS-acrylimide gel analysis of recombinant LF secretion and purification.

FIG. 6 depicts the cDNA sequence for human lactoferrin.

DETAILED DESCRIPTION OF THE INVENTION DEFINITIONS

Figure 1:
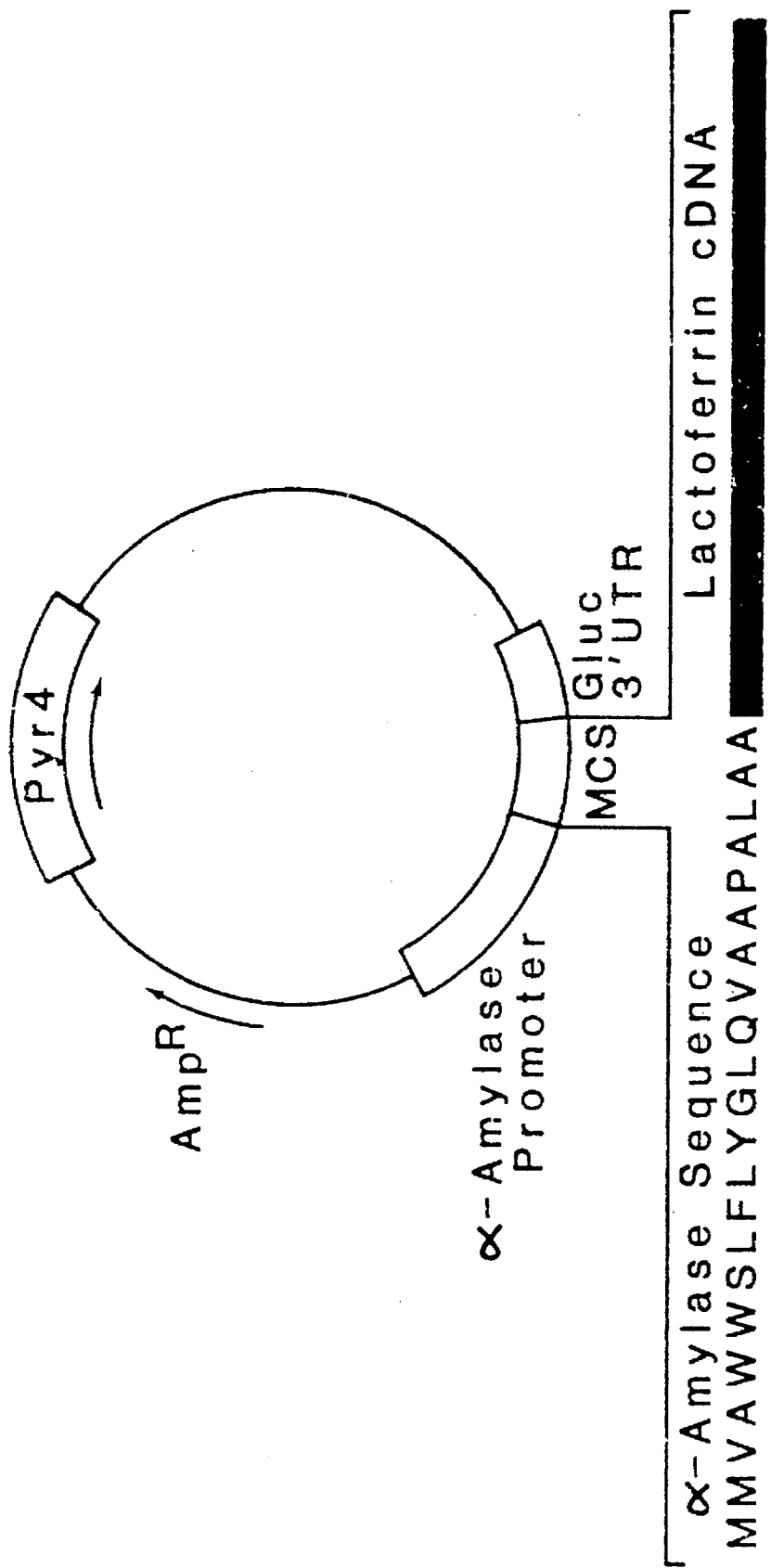
FIG. 1 depicts a schematic representation of the aspergillus oryzae expression plasmid, pAhlfg.

For the purposes of the present application, the term "transferrin family" means a family of iron transferring proteins including serum transferrin, ovotransferrin and lactoferrin. These proteins are all structurally related.

For the purposes of the present application, the term "vector(s)" means plasmid vehicle to allow insertion, propagation and expression of lactoferrin cDNA.

For the purposes of the present application, the term "host(s)" means any eucaryotic cell that will allow integration of the lacatoferrin expression plasmid into its genome.

For the purposes of the present application, the term "promotor(s)" means regulatory DNA sequences that controls transcription of the lactoferrin cDNA.

For the purposes of the present application, the term "multiple cloning cassette" means a DNA fragment containing restriction enzyme cleavage sites for a variety of enzymes allowing insertion of a variety of cDNAs.

For the purposes of the present application, the term "transformation" means uptake of plasmid by a relevant eucaryotic cell.

For the purposes of the present application, the term "iron binding capacity" means ability to bind $^{59}Fe$. Fully functional lactoferrin can bind two atoms of iron per molecule of LF.

For the purposes of the present application, the term "biological activity/biological active" means biological activity of lactoferrin as measured by its ability to bind iron. The lactoferrin protein functions as an iron transfer protein and must bind iron to be biologically active.

All literature references cited in this specification are hereby expressly incorporated by reference.

The following examples are given for the purposes of illustrating various embodiments of the present invention and are not meant to be limitations of the present invention in any form.

EXAMPLE 1

Fungal Strains and Transformation

The pyrG mutant strain used in these studies was derived from *A. oryzae* (A07 11488). The pyrG gene from *A. oryzae* was mutated with 4-nitroquinoline-1-oxide. The Aspergillus transformation was carried out by a modification of the procedure of Osmani, et al., *J. Cell. Biol.* 104:1495–1504 (1987). Conidia (1×10$^6$/ml) were inoculated into 50 ml of YG medium (0.5% yeast extract 2% glucose) containing 5 mM uracil and 10 mM uridine. Growth was at 32° C. for 14–16 hours until a germ tube was visible. The germinated conidia were harvested by centrifugation and resuspended in 40 ml of lyric mix containing 0.4M ammonium sulphate, 50 mM potassium citrate (pH 6.0), 0.5% yeast extract, 0.12 g novozyme, 0.1 g Driselase, 100 µl β-glucuronidase, 0.5% sucrose and 10 mM MgSO$_4$. Protoplasting was for 2–3 hours at 32° C. and 150 rpm. Following protoplasting, filtration using sterile miracloth was necessary to remove any undigested mycelia. The protoplasts were harvested by centrifugation and washed twice with 10 ml of 0.4M ammonium sulphate, 1% sucrose and 50 mM potassium citrate (pH 6.0) at 4° C., resuspended in 1 ml of 0.6 M KCl; 50 mM CaCl; 10 mM Tris-HCl (pH 7.5) and placed on ice. The transformation was performed immediately following the protoplast preparation. Aliquots (100 µl) of the protoplast were added to 3 µg of DNA and 50 µl of 40% polyethylene glycol (PEG) 6000, 50 mM CaCl$_2$, 0.6M KCl and 10 mM Tris-HCl,(pH 7.5). The samples were incubated on ice for fifteen minutes after which an additional i ml of the PEG solution was added and incubation at room temperature was continued for thirty minutes. Aliquots of this mixture were plated in 3 mls of 0.7% minimal media, supplemented with 0.4% ammonium sulphate onto plates containing the same but solidified with 2% agar. All subsequent growth was at 32° C.

EXAMPLE 2

Plasmid Construction

A schematic representation of the expression plasmid is shown in FIG. 1. The complete cDNA encoding human LF was repaired using the Klenow fragment of DNA polymerase I and subcloned into AccI digested and repaired pGEM4 to generate pGEMhLFc. In order to remove the LF signal sequence and generate a 5' end in frame with the α-amylase sequences, a 252 base pair lactoferrin fragment (nt 69–321) containing HindlI/AccI ends was obtained by polymerase chain reaction (PCR) amplification of pGEMhLFc plasmid DNA. The oligo primers used were as follows: the 5' end oligonucleotide as shown in SEQ. ID. No. 1:

(CTGGGTCGACGTAGGAGAAGGAGTGT-TCAGTGGTGC)

and the 3' end oligonucleotide as shown in SEQ. ID. No. 2:

(GCCGTAGACTTCCGCCGCTACAGG).

This PCR fragment was digested with HindII and AccI and was subcloned into Hind 11/AccI digested pGEMhLFC generating pGEMhLF. A 681 base pair α-amylase fragment with Asp718/PvuII ends encoding the promotor, signal sequence and the alanine residue from the start of the mature α-amylase II gene, was obtained by PCR amplification of *A. oryzae* genomic DNA. The oligo primers were as follows: the 5' end oligonucleotide as shown in SEQ. ID. No. 3:

(GAGGTACCGAATTCATGGTGTTTTGAT-CATTTTAAATTTTTATAT)

and the 3' end oligonucleotide as shown in SEQ. ID. No. 4:

(AGCAGCTGCAGCCAAAGCAGGTGCCGC-GACCTGAAGGCCGTACAG).

The amplified DNA was digested with Asp718 and PvuII and subcloned into Asp718Hind11 digested pGEMhLF. The resulting plasmid (pGEMAhLF) was digested with EcoRI and the resulting 2.8 kb α-amylase-lactoferrin fragment was subcloned into a unique EcoRI site in pAL3 according to the method of generating pAhLF*. Synthetic oligonucleotide were used to provide the last five carboxy terminal codons of lactoferrin (nt 2138–2153) missing in pAhLF* and also to provide the first 180 bp of 3' untranslated sequences from the *A. niger* glucoamylase gene. The resulting plasmid (pAhLFG) was used to transform the A oryzae pyrG mutant strain.

With reference to FIG. 1, *Aspergillus oryzae* expression plasmid, pAhLFG contains 681 bp of 5'-flanking sequence of the *A. oryzae* AMY11 gene which includes the signal sequence and first codon of mature α-amylase. The cDNA coding for mature human lactoferrin is subcloned in frame downstream from these sequences allowing recombinant protein production by the addition of starch to the growth medium. The *Aspergillus niger* glucoamylase 3' untranslated region provides the transcription terminator and polyadenylation signals. The plasmid also contains the Neurospora crassa pyr4 selectable marker and an ampicillin resistance gene.

The plasmid construct (pAhLFG) used for expression of human LF contains a 681 bp fragment that encodes the promotor and secretory signal peptide of the *A. oryzae* α-amylase II gene (AMY11). The signal sequence also contains the codon for alanine from the start of the α-amylase mature protein generating the signal sequence cleavage site (Leu Ala Ala) recognizable by an endogenase α-amylase peptidase. A human lactoferrin cDNA fragment encoding the mature protein was subcloned in frame immediately downstream from the AMYII sequences, placing it under the control of this highly efficient starch inducible promoter. In order to stabilize the transcribed human LF mRNA, a 180 bp fragment encoding the 3' untranslated region of the glucoamylase gene from *Aspergillus niger* was ligated into a unique BamHI site in the multiple cloning cassette, immediately downstream of the human LF cDNA providing the transcription terminator and polyadenylation signals. The plasmid also contains the Neurospora crassa Pyr4 selectable marker which complements a pyrG auxotrophic mutation of *A. oryzae* and allows for selection of spores that have been transformed with the plasmid by growth in the absence of uridine.

EXAMPLE 3

Genomic DNA Manipulation

*A. oryzae* DNA was isolated from 200 mg of lyophilized mycelia as described by Rafmussen, et al., *J. Biol. Chem.*, 265:13767–13775 (1990). The DNA was digested with EcoRI, size fractionated on a 0.8% agarose gel and transferred to nitrocellulose. Prehybridization and hybridization of the nitrocellulose filter for Southern analysis were performed in 6XSSC, 0.1% SDS and 0.5% dried milk at 65° C. for 16 hours. Hybridization solution contained $1 \times 10^7$ cpm $^{32}$P-labelled lactoferrin cDNA probe (2.1 Kb). The filter was washed in 2XSSC, 0.5% SDS at room temperature for 30 minutes followed by two washes in 0.5X SSC, 0.5% SDS at 68° C. for 30 minutes. The filter was dried, exposed at −70° C. for two hours and developed by autoradiography.

Figure 2:
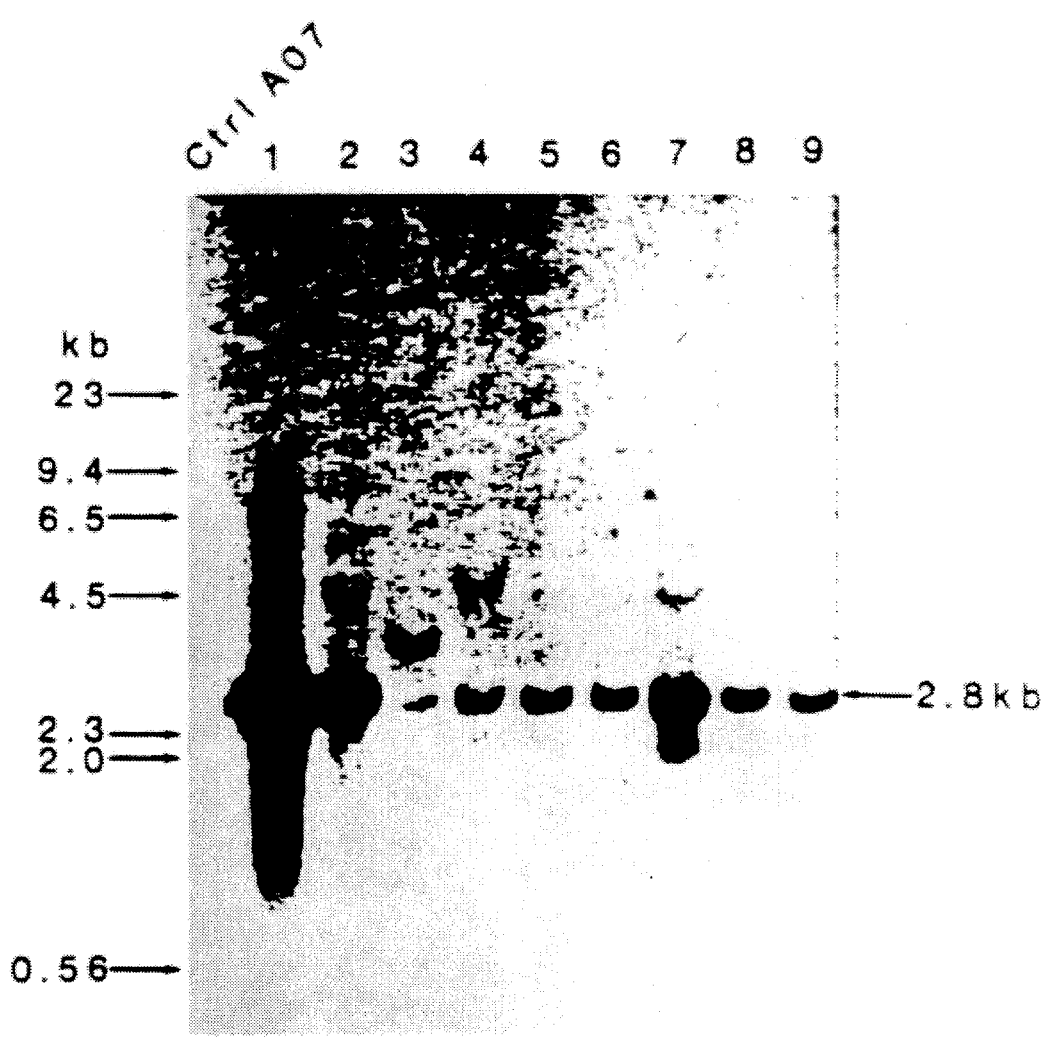
FIG. 2 shows a southern blot analysis of transformed aspergillus oryzae strains.

With reference to FIG. 2, Southern blot analysis was performed on transformed *Aspergillus oryzae* strains. Genomic DNA from individual transformants and control AO7 were hybridized with a radiolabelled hLF cDNA probe (2.1 kb). The arrow points to a radiolabelled fragment (2.8 kb) generated upon EcoR1 digestion of the expression plasmid which is present in all the transformants (#1–9) but is absent in control untransformed AO7. Molecular weights of bacteriophage lambda Hind 111 fragments are indicated at the left.

EXAMPLE 4

Northern Analysis

RNA was isolated from lyophilized mycelia (200 mg) using commercially available RNazol B (Biotecx Laboratories, INC, Houston, Tx.) according to the manufacturers instructions. Total RNA (20 µg) was electrophoresed in a 0.8% agarose gel containing 2.2M formaldehyde. The RNA was transferred to nitrocellulose and hybridized with either a 2.1 kb lactoferrin cDNA or a 1.8 kb genomic α-amylase fragment corresponding to the coding region of the α-amylase 11 gene. The probes were $^{32}$p, labelled by nick translation (specific activity $2 \times 10^8$ cpm/ug). Hybridization was carried out 2xSSC, 0.05% dried milk at 65° C. over an ice with $2 \times 10^6$ cpm probe/ml.

Washes were identical to those employed in the Southern analysis. The filters were dried, exposed at −70° C. for two hours and developed by autoradiography. RNA dot blots were performed using nitrocellulose membrane and the manifold dot blot system. Hybridization and washing conditions were as described above for Southern analysis. Radioactivity was quantitated using the betagon blot analyzer.

Recombinant production of lactoferrin protein has been described in its preferred embodiment. However, it could also be produced in a number of other sources such as fungal sources such as saccharomyces cerevisiae or pichia pastorsis or insect cells such as SF9.

With reference to FIG. 3, RNA analysis of transformant versus control AO7 was performed. In Panel A, Northern analysis of RNA (20 µg) from control AO7 and transformant #1 hybridized with radiolabelled human LF cDNA. Human LF mRNA (2.3 kb) was detected in the transformant #1 but not in the control untransformed AO7. The positions of the 28s and 18s rRNA bands are indicated on the left. In Panel B, Dot blots of RNA (5 and 10 µg) from control AO7 versus transformant #1 using a radiolabelled α-amylase genomic DNA probe. In Panel C, Dot blots of RNA (5 and 10µg from control AO7 and transformant #1 using radiolabelled human LF cDNA probe as illustrated.

Northern analysis was performed to determine if lactoferrin mRNA was transcribed correctly and efficiently in *A. oryzae* under the regulatory control elements of our expression plasmid. Spores ($1 \times 10^6$/ml) from transformant #1 and from control untransformed spores were inoculated into fungal medium containing 1.5% glucose as carbon source and grown at 30° C. for 48 hours in small shake flask cultures. The cultures were washed and reinoculated into fungal medium containing 3% starch to induce transcription of the human LF mRNA. After 24 hours, the cells were harvested and RNA was isolated. Total RNA (20 µg) was size fractionated on a 1.0% agarose gel containing 2.2M formaldehyde and blotted on nitrocellulose.

Human lactoferrin mRNA was detected using 32p labelled human LF cDNA (2.0 kb) probe. Hybridization with human LF radiolabelled cDNA probe detected a specific radiolabelled band at the correct size for lactoferrin mRNA (2.3kb) in the transformant but not in the control untransformed strain (FIG. 3A). Quantitation of mRNA levels by dot assay showed comparable levels of expression of endogenous α-amylase rRNA between control AO7 and transformant #1 (FIG. 3B). In addition, similar levels of expression of α-amylase and human LF mRNA were seen in transformant #1 (FIG. 3B and 3C).

EXAMPLE 5

Purification of Recombinant Human LF

LF was Purified from the Growth Medium Using CM Sephadex C50 essentially as described by Stowell, et al., *Biochem J.*, 276:349–59 (1991). The column was preequilibrated with 500 ml of 0.025M Tris HCl, pH 7.50 1M NaCl. The pH of the culture medium was adjusted to pH 7.4 before applying to the preequilibrated column. The column was washed with 500 ml of equilibration buffer and followed by a linear salt gradient from 0.1 to 1.1M NaCl. Fractions (7 ml total) were assayed for lactoferrin content and purity using SDS/PAGE and silver staining. Fractions containing LF were dialyzed against 0.025M Tris HCl, pH 7.5/0.1M NaCl and lyophilized.

EXAMPLE 6

Quantitation of Human LF

Recombinant lactoferrin was quantitated using an ELISA assay essentially as described by Vilja et al., *J. Immunol. Methods*, 76:73–83 (1985). A sensitivity of 5 ng of lactoferrin was obtained using the noncompetitive Avidin-biotin assay. Human LF isolated from breast milk (Sigma) was used as standard. Biotinylated human lactoferrin IgG was obtained from Jackson Immunoresearch laboratories, West Grove, Pa.

EXAMPLE 7

N-terminal Sequencing

Five μg of purified recombinant human LF was resolved on an SDS-polyacrylamide gel and transferred to Problott, a polyvinylidene difluride-type membrane, following manufacturers instructions (Applied Biosystems). Human LF was detected with Comassie Brilliant Blue staining and destained. This human LF band was excised, washed thoroughly with distilled $H_2O$ and air-dried. The N-terminal amino acid sequence of the first ten amino acids of human LF was determined by the automated Edman degradation procedure using an applied Biosystems Pulsed-liquid phase sequencer (Model 477A).

With reference to FIG. 4, panel A illustrates a Silver stained SDS-polyacrylamide gel analysis of recombinant human LF secretion and purification. Lane 1 contains breast milk human LF standard (500 ng). Lanes 2 and 3 contain samples of the growth medium (40 μg) from induced control AO7 and transformant #1 respectively. Lanes 4–8 contain 100 μl aliquots of eluted fractions (#25, 30, 35, 40, and 45 respectively) collected from the CM-sephadex purification of recombinant LF from the growth medium of transformant #1. The position of the molecular weight markers (BioRad laboratories Richmond, Calif.) are indicated on the left. Sizes are given in kilodaltons. Panel B illustrates a Western immunoblot analysis of duplicate samples as described in panel A using a specific polyclonal antibody directed against human LF with detection with $^{125}$-protein A. Panel C illustrates #6 N-terminal amino acid sequence of recombinant human LF. Recombinant human LF was sequenced from the N-terminus through 10 residues and is identical to breast milk human LF with the exception of the additional alanine generated in our construction to provide the α-amylase signal sequence cleavage site.

EXAMPLE 8

Deglycosylation

Deglycosylation was performed using N-glycosidase F (Boehringer Mannheim). *A. oryzae* growth medium containing 0.5 μg lactoferrin was denatured for 3 minutes at 100° C. in the presence of 0.01% SDS. Standard LF from human milk was treated similarly. The samples were subsequently placed on ice for five minutes. N-glycosidase F reactions were conducted in 0.4M sodium phosphate, (pH 6.8); 0.08% Triton; 0.1% β-mercaptoethanol and 1 unit of enzyme and incubated at 37° C. for sixteen hours. PAGE and western analysis was performed using an IgG specifically directed against human lactoferrin to detect an increase in mobility of digested samples.

With reference to FIG. 5, recombinant human LF was characterized. Panel A illustrates the deglycosylation of lactoferrin. Western analysis of glycosylated and deglycosylated lactoferrin using a specific polyclonal antibody was directed against human lactoferrin with detection with $^{125}$I-protein A. The first panel contains authentic breast milk human LF (500 ng) untreated (−) and treated (+) with N glycosidase F. The second panel contains purified recombinant human LF (500 ng) untreated (−) and treated (+) with N-glycosidase F. The size of glycosylated human LF is indicated with the arrow. Panel B illustrates a functional analysis of recombinant lactoferrin with regard to iron-binding capacity. Panel A and B show the $^{59}$Fe filter binding assay of duplicate samples of authentic breast milk human LF and purified recombinant human LF, respectively, at the concentrations indicated. The first lane in both panels contain BSA (5 μg) as a negative control.

Figure 5A:
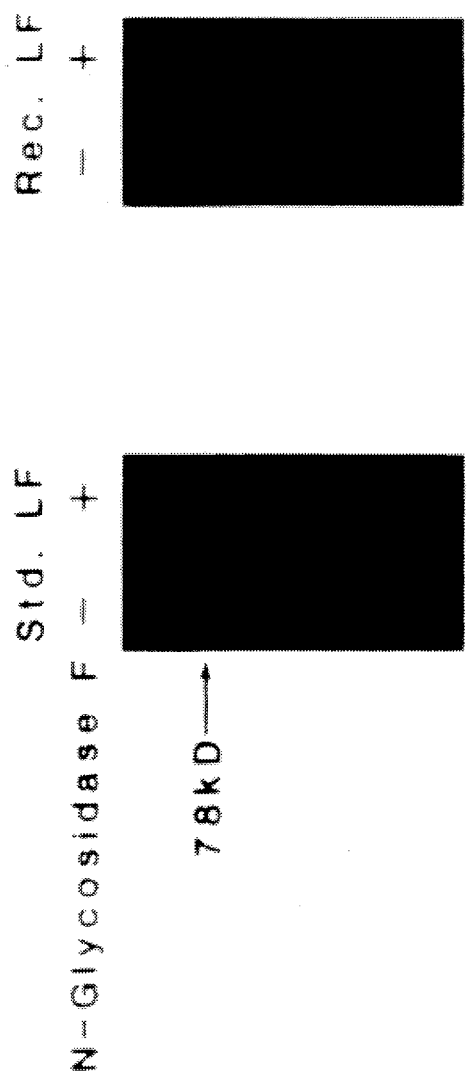
FIG. 5 illustrates the characterization of recombinant human LF.

Lactoferrin contains two N-acetyllactamine type glycans attached through N-glycosidic linkages. To determine if recombinant lactoferrin was glycosylated correctly, the protein was treated with N-glycosidase F, resolved on SDS-polyacrylamide electrophoresis, transferred to nitrocellulose and probed using a specific IgG directed against human lactoferrin (FIG. 5A). N-glycosidase F hydrolyses at the glycosylamine linkage generating a carbohydrate free peptide of smaller molecular weight. Comparison of recombinant LF with purified LF from human milk, illustrates that both proteins co-migrate upon digestion with N-glycosidase F suggesting that the recombinant protein has a glycosylation pattern similar to native LF.

Figure 5B:
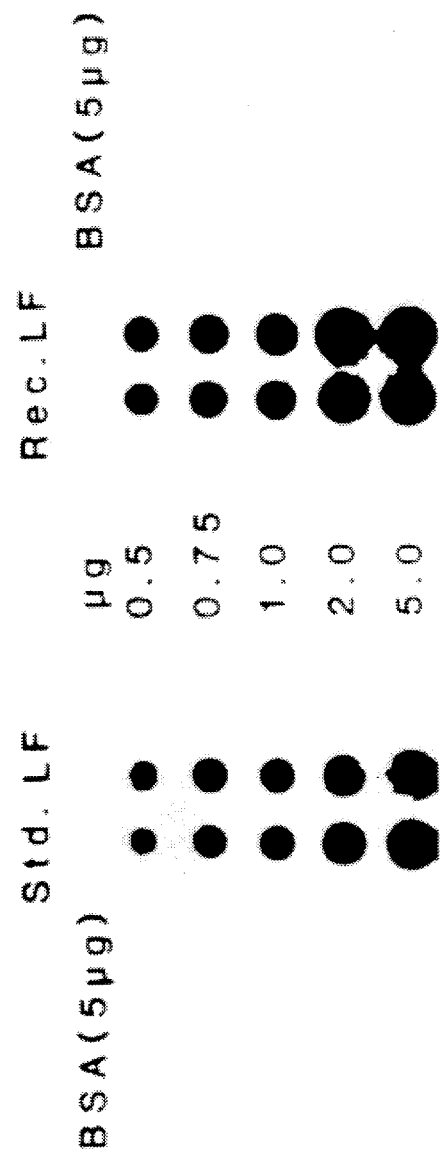

Lactoferrin has a bilobal structure with each lobe having the capacity to bind tightly, but reversibly, one $Fe^{3+}$ ion. The iron-binding properties of lactoferrin are crucial for its functional roles. To test if recombinant human LF expressed and secreted in A oryzae has an iron binding capacity similar to authentic lactoferrin, an $^{59}$Fe micro filter binding assay was developed. Purified human lactoferrin isolated from the growth medium of transformant #1 was dialyzed against 0.1M citric acid (pH 2.0) to generate apo-human LF. Native lactoferrin from human milk was treated similarly. Excess $^{59}$Fe (0.2 mCi) was added to these samples in an equal volume of i M bicarbonate, followed by incubation at 37° C. for 30 minutes. Samples were applied to nitrocellulose membrane and washed several times with bicarbonate. The filter was visualized by autoradiography and Fe-binding was quantitated using a betagon blot analyzer. As illustrated in FIG. 5B, both recombinant and native LF showed a similar level of iron binding at all concentrations tested. The results demonstrate that recombinant human LF Is indistinguishable from native human LF in its capacity to bind iron.

With reference to FIG. 6, the complete cDNA sequence for human lactoferrin protein is depicted. The cDNA coding for lactoferrin is used to create plasmids and transform eucaryotic cells and to produce the lactoferrin protein.

Strains of aspergillus used in the present invention are auxotrophic routants that contain a defective pyr 4 gene that results in an inability to synthesis orotidine 5' phosphate (OMP) decarboxylase. The enzyme is required for uridine synthesis. The strain cannot grow on media lacking uridine. The plasmid contains a selectable marker, i.e., a sequence that encodes the gene for OMP decarboxylase. Uptake of the plasmid by the aspergillus can therefore be selected for by growth on media lacking uridine. The aspergillus is transformed by the plasmid such that it can grow on the uridine deficient media.

In one embodiment of the present invention, biologically active recombinant lactoferrin protein is produced. This method comprises synthesizing sequences containing a selectable marker gene, a promotor, a transcription termination sequence and a linker sequence. Subsequently, the sequences are cloned to form a plasmid and the plasmid is digested with a restriction endonuclease. A cDNA coding for lactoferrin is inserted into a restriction site and eucaryotic cells are then transformed with the plasmid expressing the lactoferrin cDNA.

The selectable marker gene useful in the method of the present invention may be any that permits isolation of cells

9 transformed with a lactoferrin cDNA plasmid. Preferably, the selectable marker gene is selected from pyr4, pyrG, argB, trpC and amdS.

The promotor useful in the present invention may be any that allows regulation of the transcription of the lactoferrin cDNA. Preferably, the promotor is selected from the group of alcohol dehydrogenase, argB, α-amylase and glucoamylase.

The transcription termination sequence useful in the present method may be any that allows stabilization of the lactoferrin mRNA. Preferably, the transcription termination sequence is derived from α-amylase, glucoamylase, alcohol dehydrogenase or benA.

The linker sequence useful in the present method may be any that contains a translation initiation codon, a secretory signal and a restriction enzyme cleavage site. Preferably, the linker element is derived from α-amylase, glucoamylase or lactoferrin.

The eucaryotic cells useful in the present invention are any that allow for integration of a plasmid comprising the lactoferrin cDNA and expression of the lactoferrin cDNA.

10

Preferably, the eucaryotic cells are fungal cells or insect cells. Insect cells such as SF9 are useful in the method of the present invention. More preferably, the fungal cells are yeast cells. Most preferably, the eucaryotic cells useful in the present invention are aspergillus strains, such as *A. oryzae, A. Niger, A. Nidulans* and *A. Awamori*.

In conclusion, it is seen that the present invention and the embodiments disclosed herein are well adapted to carry out the objectives and obtain the end set forth in this application. Certain changes can be made in the method and apparatus without parting from the spirit and scope of this invention. It is realized that changes are possible and that it is further intended that each element or step presided in any of the filing claims is to be understood as to referring to all equivalent elements or steps for accomplishing the essentially the same results in substantially the same or equivalent manner. It is intended to cover the invention broadly in whatever form its principles may be utilized. The present invention, therefore, is well adapted to carry out the objects and obtain the ends and advantages mentioned, as well as others inherent therein.

What is claimed is:

1. A process for a producing human lactoferrin comprising the following steps:

1) culturing an Aspergillus cell in a nutrient medium under conditions suitable for the expression of human lactoferrin by said Aspergillus cell and the secretion of said human lactoferrin protein into said medium, wherein said Aspergillus cell is transformed with an expression vector that comprises a fungal promoter sequence operably linked to a polypeptide-encoding nucleotide sequence, said polypeptide-encoding sequence comprising a secretory signal peptide-encoding nucleotide sequence fused to a polynucleotide encoding a human lactoferrin protein and providing a single open reading frame, said vector further comprising nucleotide sequence elements regulating translation of said polypeptideencoding nucleotide sequence, and, 2) isolating said secreted human lactoferrin protein from said medium.

2. The process of claim 1 wherein said fungal cell Aspergillus is selected from the group consisting of *A. oryzae, A. niger, A. nidulans* and *A. awamori.*

3. The process of claim 1, wherein said promoter is selected from the genes of the group consisting of alcohol dehydrogenase, argB, α-amylase, glucoamylase, and benA.

4. The process of claim 1, wherein the polynucleotide sequence encloding a human peptide-encoding nucleotide is the nucleotide sequence of SEQ ID NO:1 between nucleotide positions 18 and 2150, inclusive.

5. The process of claim 1, wherein the encoded human lactoferrin protein has the amino acid sequence of SEQ. ID NO:2.

6. The process of claim 1, wherein said vector further comprises a selectable marker gene, and a transcription termination sequence.

7. The process of claim 6, wherein said selectable marker gene is selected from the genes of the group consisting of pyr4, pyrG, amdS, argB and trpC.

8. The process of claim 6, wherein said transcription termination sequence is selected from the genes of the group consisting of α-amylase, glucoamylase, alcohol dehydrogenase and benA.

9. The process of claim 6, wherein said secretory signal peptide-encoding nucleotide sequence is selected from the genes of the group consisting of α-amylase, glucoamylase and lactoferrin.

10. A method of isolating human lactoferrin from fungal nutrient medium which comprises culturing a transformed fungal cell selected from the group consisting of *Aspergillus orzae, Aspergillus nidulans, Aspergillus niger,* and *Aspergillus awamori,* said transformed fungal cell comprising a recombinant vector, said vector comprising a fungal promoter sequence operably linked to a polypeptide-encoding nucleotide sequence, wherein said polypeptide-encoding sequence comprises a nucleotide sequence encoding a secretory signal peptide fused to a polynucleotide encoding a human lactoferrin protein having the amino acid sequence of SEQ ID NO:2, and a transcription termination sequence, wherein said transformed cell is cultured for a sufficient time in a suitable nutrient medium until human lactoferrin protein is formed, and wherein human lactoferrin is secreted into the nutrient medium and isolated therefrom.

11. The method of claim 10 wherein the plasmid vector is further defined as comprising a pyr4 selectable marker gene, a promoter from the alpha-amylase gene, a transcription termination sequence from the glucoamylase gene, and a nucleotide sequence encoding a secretory signal peptide of an alpha-amylase gene.

12. A recombinant expression vector having a transcriptional unit comprising a fungal promoter sequence regulating gene expression in an Aspergillus cell, said promoter sequence operably linked to a polypeptide-encoding nucleotide sequence that comprises a polynucleotide encoding a human lactoferrin protein, nucleotide sequence elements regulating translation of said polypeptide-encoding nucleotide sequence, and, optionally, a transcription termination sequence.

13. The vector of claim 12, wherein said promoter is selected from the genes of the group consisting of alcohol dehydrogenase, argB, α-amylase, glucoamylase, and benA.

14. The vector of claim 12, wherein said transcription termination sequence is selected from the genes of the group consisting of α-amylase, glucoamylase, alcohol dehydrogenase and benA.

15. A plasmid comprising a nucleotide sequence encoding a human lactoferrin that comprises the amino acid sequence of SEQ ID NO:2 and further comprises nucleotide sequence regulatory elements necessary for the expression of said human lactoferrin-encoding nucleotide sequence in cells of the genus Aspergillus wherein said plasmid permits the expression of a human lactoferrin having the amino acid sequence of SEQ ID NO:2 by Aspergillus fungal cells.

16. The plasmid of claim 15 further defined as having ATCC Accession Number 74222 and designated pAhLFG.

17. A fungal cell comprising the plasmid of claim 15.

18. The fungal cell of claim 17 further defined as an Aspergillus fungal cell.

19. The Aspergillus cell of claim 18, wherein the cell is *A. oryzae.*

20. The Aspergillus cell of claim 18, wherein the cell is *A. nidulans.*

21. The Aspergillus cell of claim 18, wherein the cell is *A. awamori.*

22. The Aspergillus cell of claim 18, wherein the cell is *A. niger.*

23. The fungal cell of claim 17 further defined as a yeast fungal cell.

24. The yeast cell of claim 23, wherein said cell is further defined as *Saccharomyces cerevesiae* or *Pichia pastoris.*

\* \* \* \* \*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2360 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_RNA
        ( B ) LOCATION: 18..2153
        ( C ) IDENTIFICATION METHOD: experimental
        ( D ) OTHER INFORMATION: /product="lactoferrin"
            / evidence=EXPERIMENTAL ( i x ) FEATURE:
        ( A ) NAME/KEY: CDS
        ( B ) LOCATION: 18..2153

( x i ) SEQUENCE DESCRIPTION: SEQ ID NO:1:

```
GAATTCGAC  CGCAGAC  ATG  AAA  CTT  GTC  TTC  CTC  GTC  CTG  CTG  TTC  CTC          50
                    Met  Lys  Leu  Val  Phe  Leu  Val  Leu  Leu  Phe  Leu
                     1                  5                            10

GGG  GCC  CTC  GGA  CTG  TGT  CTG  GCT  GGC  CGT  AGG  AGA  AGG  AGT  GTT  CAG     98
Gly  Ala  Leu  Gly  Leu  Cys  Leu  Ala  Gly  Arg  Arg  Arg  Arg  Ser  Val  Gln
              15                        20                      25

TGG  TGC  ACC  GTA  TCC  CAA  CCC  GAG  GCC  ACA  AAA  TGC  TTC  CAA  TGG  CAA    146
Trp  Cys  Thr  Val  Ser  Gln  Pro  Glu  Ala  Thr  Lys  Cys  Phe  Gln  Trp  Gln
              30                        35                      40

AGG  AAT  ATG  AGA  AGA  GTG  CGT  GGC  CCT  CCT  GTC  AGC  TGC  ATA  AAG  AGA    194
Arg  Asn  Met  Arg  Arg  Val  Arg  Gly  Pro  Pro  Val  Ser  Cys  Ile  Lys  Arg
              45                        50                      55

GAC  TCC  CCC  ATC  CAG  TGT  ATC  CAG  GCC  ATT  GCG  GAA  AAC  AGG  GCC  GAT    242
```

|     |     |     |     |     |     |     |     |     |     |     |     |     |     |     |     |
| --- | --- | --- | --- | --- | --- | --- | --- | --- | --- | --- | --- | --- | --- | --- | --- |
| Asp | Ser | Pro | Ile | Gln | Cys | Ile | Gln | Ala | Ile | Ala | Glu | Asn | Arg | Ala | Asp |
| 60  |     |     |     | 65  |     |     |     |     | 70  |     |     |     |     | 75  |     |

| GCT | GTG | ACC | CTT | GAT | GGT | GGT | TTC | ATA | TAC | GAG | GCA | GGC | CTG | GCC | CCC | 290 |
| --- | --- | --- | --- | --- | --- | --- | --- | --- | --- | --- | --- | --- | --- | --- | --- | --- |
| Ala | Val | Thr | Leu | Asp | Gly | Gly | Phe | Ile | Tyr | Glu | Ala | Gly | Leu | Ala | Pro | |
|     |     |     |     | 80  |     |     |     | 85  |     |     |     |     |     | 90  |     | |

| TAC | AAA | CTG | CGA | CCT | GTA | GCG | GCG | GAA | GTC | TAC | GGG | ACC | GAA | AGA | CAG | 338 |
| --- | --- | --- | --- | --- | --- | --- | --- | --- | --- | --- | --- | --- | --- | --- | --- | --- |
| Tyr | Lys | Leu | Arg | Pro | Val | Ala | Ala | Glu | Val | Tyr | Gly | Thr | Glu | Arg | Gln | |
|     |     |     | 95  |     |     |     |     | 100 |     |     |     |     | 105 |     |     | |

| CCA | CGA | ACT | CAC | TAT | TAT | GCC | GTG | GCT | GTG | GTG | AAG | AAG | GGC | GGC | AGC | 386 |
| --- | --- | --- | --- | --- | --- | --- | --- | --- | --- | --- | --- | --- | --- | --- | --- | --- |
| Pro | Arg | Thr | His | Tyr | Tyr | Ala | Val | Ala | Val | Val | Lys | Lys | Gly | Gly | Ser | |
|     |     | 110 |     |     |     |     | 115 |     |     |     |     | 120 |     |     |     | |

| TTT | CAG | CTG | AAC | GAA | CTG | CAA | GGT | CTG | AAG | TCC | TGC | CAC | ACA | GGC | CTT | 434 |
| --- | --- | --- | --- | --- | --- | --- | --- | --- | --- | --- | --- | --- | --- | --- | --- | --- |
| Phe | Gln | Leu | Asn | Glu | Leu | Gln | Gly | Leu | Lys | Ser | Cys | His | Thr | Gly | Leu | |
|     | 125 |     |     |     |     | 130 |     |     |     |     | 135 |     |     |     |     | |

| CGC | AGG | ACC | GCT | GGA | TGG | AAT | GTG | CCT | ATA | GGG | ACA | CTT | CGT | CCA | TTC | 482 |
| --- | --- | --- | --- | --- | --- | --- | --- | --- | --- | --- | --- | --- | --- | --- | --- | --- |
| Arg | Arg | Thr | Ala | Gly | Trp | Asn | Val | Pro | Ile | Gly | Thr | Leu | Arg | Pro | Phe | |
| 140 |     |     |     |     | 145 |     |     |     |     | 150 |     |     |     |     | 155 | |

| TTG | AAT | TGG | ACG | GGT | CCA | CCT | GAG | CCC | ATT | GAG | GCA | GCT | GTG | GCC | AGG | 530 |
| --- | --- | --- | --- | --- | --- | --- | --- | --- | --- | --- | --- | --- | --- | --- | --- | --- |
| Leu | Asn | Trp | Thr | Gly | Pro | Pro | Glu | Pro | Ile | Glu | Ala | Ala | Val | Ala | Arg | |
|     |     |     |     | 160 |     |     |     |     | 165 |     |     |     |     | 170 |     | |

| TTC | TTC | TCA | GCC | AGC | TGT | GTT | CCC | GGT | GCA | GAT | AAA | GGA | CAG | TTC | CCC | 578 |
| --- | --- | --- | --- | --- | --- | --- | --- | --- | --- | --- | --- | --- | --- | --- | --- | --- |
| Phe | Phe | Ser | Ala | Ser | Cys | Val | Pro | Gly | Ala | Asp | Lys | Gly | Gln | Phe | Pro | |
|     |     |     | 175 |     |     |     |     | 180 |     |     |     |     | 185 |     |     | |

| AAC | CTG | TGT | CGC | CTG | TGT | GCG | GGG | ACA | GGG | GAA | AAC | AAA | TGT | GCC | TTC | 626 |
| --- | --- | --- | --- | --- | --- | --- | --- | --- | --- | --- | --- | --- | --- | --- | --- | --- |
| Asn | Leu | Cys | Arg | Leu | Cys | Ala | Gly | Thr | Gly | Glu | Asn | Lys | Cys | Ala | Phe | |
|     |     | 190 |     |     |     |     | 195 |     |     |     |     | 200 |     |     |     | |

| TCC | TCC | CAG | GAA | CCG | TAC | TTC | AGC | TAC | TCT | GGT | GCC | TTC | AAG | TGT | CTG | 674 |
| --- | --- | --- | --- | --- | --- | --- | --- | --- | --- | --- | --- | --- | --- | --- | --- | --- |
| Ser | Ser | Gln | Glu | Pro | Tyr | Phe | Ser | Tyr | Ser | Gly | Ala | Phe | Lys | Cys | Leu | |
|     | 205 |     |     |     |     | 210 |     |     |     |     | 215 |     |     |     |     | |

| AGA | GAC | GGG | GCT | GGA | GAC | GTG | GCT | TTT | ATC | AGA | GAG | AGC | ACA | GTG | TTT | 722 |
| --- | --- | --- | --- | --- | --- | --- | --- | --- | --- | --- | --- | --- | --- | --- | --- | --- |
| Arg | Asp | Gly | Ala | Gly | Asp | Val | Ala | Phe | Ile | Arg | Glu | Ser | Thr | Val | Phe | |
| 220 |     |     |     |     | 225 |     |     |     |     | 230 |     |     |     |     | 235 | |

| GAG | GAC | CTG | TCA | GAC | GAG | GCT | GAA | AGG | GAC | GAG | TAT | GAG | TTA | CTC | TGC | 770 |
| --- | --- | --- | --- | --- | --- | --- | --- | --- | --- | --- | --- | --- | --- | --- | --- | --- |
| Glu | Asp | Leu | Ser | Asp | Glu | Ala | Glu | Arg | Asp | Glu | Tyr | Glu | Leu | Leu | Cys | |
|     |     |     |     | 240 |     |     |     |     | 245 |     |     |     |     | 250 |     | |

| CCA | GAC | AAC | ACT | CGG | AAG | CCA | GTG | GAC | AAG | TTC | AAA | GAC | TGC | CAT | CTG | 818 |
| --- | --- | --- | --- | --- | --- | --- | --- | --- | --- | --- | --- | --- | --- | --- | --- | --- |
| Pro | Asp | Asn | Thr | Arg | Lys | Pro | Val | Asp | Lys | Phe | Lys | Asp | Cys | His | Leu | |
|     |     |     | 255 |     |     |     |     | 260 |     |     |     |     | 265 |     |     | |

| GCC | CGG | GTC | CCT | TCT | CAT | GCC | GTT | GTG | GCA | CGA | AGT | GTG | AAT | GGC | AAG | 866 |
| --- | --- | --- | --- | --- | --- | --- | --- | --- | --- | --- | --- | --- | --- | --- | --- | --- |
| Ala | Arg | Val | Pro | Ser | His | Ala | Val | Val | Ala | Arg | Ser | Val | Asn | Gly | Lys | |
|     |     | 270 |     |     |     |     | 275 |     |     |     |     | 280 |     |     |     | |

| GAG | GAT | GCC | ATC | TGG | AAT | CTT | CTC | CGC | CAG | GCA | CAG | GAA | AAG | TTT | GGA | 914 |
| --- | --- | --- | --- | --- | --- | --- | --- | --- | --- | --- | --- | --- | --- | --- | --- | --- |
| Glu | Asp | Ala | Ile | Trp | Asn | Leu | Leu | Arg | Gln | Ala | Gln | Glu | Lys | Phe | Gly | |
|     | 285 |     |     |     |     | 290 |     |     |     |     | 295 |     |     |     |     | |

| AAG | GAC | AAG | TCA | CCG | AAA | TTC | CAG | CTC | TTT | GGC | TCC | CCT | AGT | GGG | CAG | 962 |
| --- | --- | --- | --- | --- | --- | --- | --- | --- | --- | --- | --- | --- | --- | --- | --- | --- |
| Lys | Asp | Lys | Ser | Pro | Lys | Phe | Gln | Leu | Phe | Gly | Ser | Pro | Ser | Gly | Gln | |
| 300 |     |     |     |     | 305 |     |     |     |     | 310 |     |     |     |     | 315 | |

| AAA | GAT | CTG | CTG | TTC | AAG | GAC | TCT | GCC | ATT | GGG | TTT | TCG | AGG | GTG | CCC | 1010 |
| --- | --- | --- | --- | --- | --- | --- | --- | --- | --- | --- | --- | --- | --- | --- | --- | --- |
| Lys | Asp | Leu | Leu | Phe | Lys | Asp | Ser | Ala | Ile | Gly | Phe | Ser | Arg | Val | Pro | |
|     |     |     |     | 320 |     |     |     |     | 325 |     |     |     |     | 330 |     | |

| CCG | AGG | ATA | GAT | TCT | GGG | CTG | TAC | CTT | GGC | TCC | GGC | TAC | TTC | ACT | GCC | 1058 |
| --- | --- | --- | --- | --- | --- | --- | --- | --- | --- | --- | --- | --- | --- | --- | --- | --- |
| Pro | Arg | Ile | Asp | Ser | Gly | Leu | Tyr | Leu | Gly | Ser | Gly | Tyr | Phe | Thr | Ala | |
|     |     |     | 335 |     |     |     |     | 340 |     |     |     |     | 345 |     |     | |

| ATC | CAG | AAC | TTG | AGG | AAA | AGT | GAG | GAG | GAA | GTG | GCT | GCC | CGG | CGT | GCG | 1106 |
| --- | --- | --- | --- | --- | --- | --- | --- | --- | --- | --- | --- | --- | --- | --- | --- | --- |
| Ile | Gln | Asn | Leu | Arg | Lys | Ser | Glu | Glu | Glu | Val | Ala | Ala | Arg | Arg | Ala | |
|     |     | 350 |     |     |     |     | 355 |     |     |     |     | 360 |     |     |     | |

| CGG | GTC | GTG | TGG | TGT | GCG | GTG | GGC | GAG | CAG | GAG | CTG | CGC | AAG | TGT | AAC | 1154 |
| --- | --- | --- | --- | --- | --- | --- | --- | --- | --- | --- | --- | --- | --- | --- | --- | --- |
| Arg | Val | Val | Trp | Cys | Ala | Val | Gly | Glu | Gln | Glu | Leu | Arg | Lys | Cys | Asn | |
|     | 365 |     |     |     |     | 370 |     |     |     |     | 375 |     |     |     |     | |

| CAG | TGG | AGT | GGC | TTG | AGC | GAA | GGC | AGC | GTG | ACC | TGC | TCC | TCG | GCC | TCC | 1202 |
| --- | --- | --- | --- | --- | --- | --- | --- | --- | --- | --- | --- | --- | --- | --- | --- | --- |

| | | | | | | | | | | | | | | | | |
|---|---|---|---|---|---|---|---|---|---|---|---|---|---|---|---|---|
| Gln | Trp | Ser | Gly | Leu | Ser | Glu | Gly | Ser | Val | Thr | Cys | Ser | Ser | Ala | Ser | |
| 380 | | | | | 385 | | | | | 390 | | | | | 395 | |
| ACC | ACA | GAG | GAC | TGC | ATC | GCC | CTG | GTG | CTG | AAA | GGA | GAA | GCT | GAT | GCC | 1250 |
| Thr | Thr | Glu | Asp | Cys | Ile | Ala | Leu | Val | Leu | Lys | Gly | Glu | Ala | Asp | Ala | |
| | | | | 400 | | | | | 405 | | | | | 410 | | |
| ATG | AGT | TTG | GAT | GGA | GGA | TAT | GTG | TAC | ACT | GCA | GGC | AAA | TGT | GGT | TTG | 1298 |
| Met | Ser | Leu | Asp | Gly | Gly | Tyr | Val | Tyr | Thr | Ala | Gly | Lys | Cys | Gly | Leu | |
| | | | 415 | | | | | 420 | | | | | 425 | | | |
| GTG | CCT | GTC | CTG | GCA | GAG | AAC | TAC | AAA | TCC | CAA | CAA | AGC | AGT | GAC | CCT | 1346 |
| Val | Pro | Val | Leu | Ala | Glu | Asn | Tyr | Lys | Ser | Gln | Gln | Ser | Ser | Asp | Pro | |
| | | 430 | | | | | 435 | | | | | 440 | | | | |
| GAT | CCT | AAC | TGT | GTG | GAT | AGA | CCT | GTG | GAA | GGA | TAT | CTT | GCT | GTG | GCG | 1394 |
| Asp | Pro | Asn | Cys | Val | Asp | Arg | Pro | Val | Glu | Gly | Tyr | Leu | Ala | Val | Ala | |
| | 445 | | | | | 450 | | | | | 455 | | | | | |
| GTG | GTT | AGG | AGA | TCA | GAC | ACT | AGC | CTT | ACC | TGG | AAC | TCT | GTG | AAA | GGC | 1442 |
| Val | Val | Arg | Arg | Ser | Asp | Thr | Ser | Leu | Thr | Trp | Asn | Ser | Val | Lys | Gly | |
| 460 | | | | | 465 | | | | | 470 | | | | | 475 | |
| AAG | AAG | TCC | TGC | CAC | ACC | GCC | GTG | GAC | AGG | ACT | GCA | GGC | TGG | AAT | ATC | 1490 |
| Lys | Lys | Ser | Cys | His | Thr | Ala | Val | Asp | Arg | Thr | Ala | Gly | Trp | Asn | Ile | |
| | | | | 480 | | | | | 485 | | | | | 490 | | |
| CCC | ATG | GGC | CTG | CTC | TTC | AAC | CAG | ACG | GGC | TCC | TGC | AAA | TTT | GAT | GAA | 1538 |
| Pro | Met | Gly | Leu | Leu | Phe | Asn | Gln | Thr | Gly | Ser | Cys | Lys | Phe | Asp | Glu | |
| | | | 495 | | | | | 500 | | | | | 505 | | | |
| TAT | TTC | AGT | CAA | AGC | TGT | GCC | CCT | GGG | TCT | GAC | CCG | AGA | TCT | AAT | CTC | 1586 |
| Tyr | Phe | Ser | Gln | Ser | Cys | Ala | Pro | Gly | Ser | Asp | Pro | Arg | Ser | Asn | Leu | |
| | | 510 | | | | | 515 | | | | | 520 | | | | |
| TGT | GCT | CTG | TGT | ATT | GGC | GAC | GAG | CAG | GGT | GAG | AAT | AAG | TGC | GTG | CCC | 1634 |
| Cys | Ala | Leu | Cys | Ile | Gly | Asp | Glu | Gln | Gly | Glu | Asn | Lys | Cys | Val | Pro | |
| | 525 | | | | | 530 | | | | | 535 | | | | | |
| AAC | AGC | AAT | GAG | AGA | TAC | TAC | GGC | TAC | ACT | GGG | GCT | TTC | CGG | TGC | CTG | 1682 |
| Asn | Ser | Asn | Glu | Arg | Tyr | Tyr | Gly | Tyr | Thr | Gly | Ala | Phe | Arg | Cys | Leu | |
| 540 | | | | | 545 | | | | | 550 | | | | | 555 | |
| GCT | GAG | AAT | GCT | GGA | GAC | GTT | GCA | TTT | GTG | AAA | GAT | GTC | ACT | GTC | TTG | 1730 |
| Ala | Glu | Asn | Ala | Gly | Asp | Val | Ala | Phe | Val | Lys | Asp | Val | Thr | Val | Leu | |
| | | | | 560 | | | | | 565 | | | | | 570 | | |
| CAG | AAC | ACT | GAT | GGA | AAT | AAC | AAT | GAG | GCA | TGG | GCT | AAG | GAT | TTG | AAG | 1778 |
| Gln | Asn | Thr | Asp | Gly | Asn | Asn | Asn | Glu | Ala | Trp | Ala | Lys | Asp | Leu | Lys | |
| | | | 575 | | | | | 580 | | | | | 585 | | | |
| CTG | GCA | GAC | TTT | GCG | CTG | CTG | TGC | CTC | GAT | GGC | AAA | CGG | AAG | CCT | GTG | 1826 |
| Leu | Ala | Asp | Phe | Ala | Leu | Leu | Cys | Leu | Asp | Gly | Lys | Arg | Lys | Pro | Val | |
| | | 590 | | | | | 595 | | | | | 600 | | | | |
| ACT | GAG | GCT | AGA | AGC | TGC | CAT | CTT | GCC | ATG | GCC | CCG | AAT | CAT | GCC | GTG | 1874 |
| Thr | Glu | Ala | Arg | Ser | Cys | His | Leu | Ala | Met | Ala | Pro | Asn | His | Ala | Val | |
| | 605 | | | | | 610 | | | | | 615 | | | | | |
| GTG | TCT | CGG | ATG | GAT | AAG | GTG | GAA | CGC | CTG | AAA | CAG | GTG | CTG | CTC | CAC | 1922 |
| Val | Ser | Arg | Met | Asp | Lys | Val | Glu | Arg | Leu | Lys | Gln | Val | Leu | Leu | His | |
| 620 | | | | | 625 | | | | | 630 | | | | | 635 | |
| CAA | CAG | GCT | AAA | TTT | GGG | AGA | AAT | GGA | TCT | GAC | TGC | CCG | GAC | AAG | TTT | 1970 |
| Gln | Gln | Ala | Lys | Phe | Gly | Arg | Asn | Gly | Ser | Asp | Cys | Pro | Asp | Lys | Phe | |
| | | | | 640 | | | | | 645 | | | | | 650 | | |
| TGC | TTA | TTC | CAG | TCT | GAA | ACC | AAA | AAC | CTT | CTG | TTC | AAT | GAC | AAC | ACT | 2018 |
| Cys | Leu | Phe | Gln | Ser | Glu | Thr | Lys | Asn | Leu | Leu | Phe | Asn | Asp | Asn | Thr | |
| | | | 655 | | | | | 660 | | | | | 665 | | | |
| GAG | TGT | CTG | GCC | AGA | CTC | CAT | GGC | AAA | ACA | ACA | TAT | GAA | AAA | TAT | TTG | 2066 |
| Glu | Cys | Leu | Ala | Arg | Leu | His | Gly | Lys | Thr | Thr | Tyr | Glu | Lys | Tyr | Leu | |
| | | 670 | | | | | 675 | | | | | 680 | | | | |
| GGA | CCA | CAG | TAT | GTC | GCA | GGC | ATT | ACT | AAT | CTG | AAA | AAG | TGC | TCA | ACC | 2114 |
| Gly | Pro | Gln | Tyr | Val | Ala | Gly | Ile | Thr | Asn | Leu | Lys | Lys | Cys | Ser | Thr | |
| | 685 | | | | | 690 | | | | | 695 | | | | | |
| TCC | CCC | CTC | CTG | GAA | GCC | TGT | GAA | TTC | CTC | AGG | AAG | TAAAACGAA | | | | 2160 |

```
Ser  Pro  Leu  Leu  Glu  Ala  Cys  Glu  Phe  Leu  Arg  Lys
700                 705                      710
```

| | | | | |
|---|---|---|---|---|
| GAAGATGGCC | CAGCTCCCCA | AGAAAGCCTC | AGCCATTCAC | TGCCCCCAGC | TCTTCTCCCC | 2220 |
| AGGTGTGTTG | GGGCCTTGGC | TCCCCTGCTG | AAGGTGGGGA | TTGCCCATCC | ATCTGCTTAC | 2280 |
| AATTCCCTGC | TGTCGTCTTA | GCAAGAAGTA | AATGAGAAA | TTTTGTTGAA | AAAAAAAAA | 2340 |
| AAAAAAAAAA | AAAAAAAAA | | | | | 2360 |

(2) INFORMATION FOR SEQ ID NO:2:

(i) SEQUENCE CHARACTERISTICS:
        (A) LENGTH: 711 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Lys  Leu  Val  Phe  Leu  Val  Leu  Leu  Phe  Leu  Gly  Ala  Leu  Gly  Leu
 1                  5                        10                       15

Cys  Leu  Ala  Gly  Arg  Arg  Arg  Arg  Ser  Val  Gln  Trp  Cys  Thr  Val  Ser
                20                       25                       30

Gln  Pro  Glu  Ala  Thr  Lys  Cys  Phe  Gln  Trp  Gln  Arg  Asn  Met  Arg  Arg
           35                       40                       45

Val  Arg  Gly  Pro  Pro  Val  Ser  Cys  Ile  Lys  Arg  Asp  Ser  Pro  Ile  Gln
      50                       55                       60

Cys  Ile  Gln  Ala  Ile  Ala  Glu  Asn  Arg  Ala  Asp  Ala  Val  Thr  Leu  Asp
 65                       70                       75                       80

Gly  Gly  Phe  Ile  Tyr  Glu  Ala  Gly  Leu  Ala  Pro  Tyr  Lys  Leu  Arg  Pro
                     85                       90                       95

Val  Ala  Ala  Glu  Val  Tyr  Gly  Thr  Glu  Arg  Gln  Pro  Arg  Thr  His  Tyr
                100                      105                      110

Tyr  Ala  Val  Ala  Val  Val  Lys  Lys  Gly  Gly  Ser  Phe  Gln  Leu  Asn  Glu
           115                      120                      125

Leu  Gln  Gly  Leu  Lys  Ser  Cys  His  Thr  Gly  Leu  Arg  Arg  Thr  Ala  Gly
      130                      135                      140

Trp  Asn  Val  Pro  Ile  Gly  Thr  Leu  Arg  Pro  Phe  Leu  Asn  Trp  Thr  Gly
145                       150                      155                      160

Pro  Pro  Glu  Pro  Ile  Glu  Ala  Ala  Val  Ala  Arg  Phe  Phe  Ser  Ala  Ser
                165                      170                      175

Cys  Val  Pro  Gly  Ala  Asp  Lys  Gly  Gln  Phe  Pro  Asn  Leu  Cys  Arg  Leu
           180                      185                      190

Cys  Ala  Gly  Thr  Gly  Glu  Asn  Lys  Cys  Ala  Phe  Ser  Ser  Gln  Glu  Pro
      195                      200                      205

Tyr  Phe  Ser  Tyr  Ser  Gly  Ala  Phe  Lys  Cys  Leu  Arg  Asp  Gly  Ala  Gly
210                      215                      220

Asp  Val  Ala  Phe  Ile  Arg  Glu  Ser  Thr  Val  Phe  Glu  Asp  Leu  Ser  Asp
225                      230                      235                      240

Glu  Ala  Glu  Arg  Asp  Glu  Tyr  Glu  Leu  Leu  Cys  Pro  Asp  Asn  Thr  Arg
                245                      250                      255

Lys  Pro  Val  Asp  Lys  Phe  Lys  Asp  Cys  His  Leu  Ala  Arg  Val  Pro  Ser
           260                      265                      270

His  Ala  Val  Val  Ala  Arg  Ser  Val  Asn  Gly  Lys  Glu  Asp  Ala  Ile  Trp
      275                      280                      285

Asn  Leu  Leu  Arg  Gln  Ala  Gln  Glu  Lys  Phe  Gly  Lys  Asp  Lys  Ser  Pro
      290                      295                      300
```

```
Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
            340                 345                 350

Lys Ser Glu Glu Val Ala Ala Arg Arg Ala Arg Val Val Trp Cys
        355                 360                 365

Ala Val Gly Glu Gln Glu Leu Arg Lys Cys Asn Gln Trp Ser Gly Leu
    370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
                405                 410                 415

Gly Tyr Val Tyr Thr Ala Gly Lys Cys Gly Leu Val Pro Val Leu Ala
            420                 425                 430

Glu Asn Tyr Lys Ser Gln Gln Ser Ser Asp Pro Asp Pro Asn Cys Val
            435                 440                 445

Asp Arg Pro Val Glu Gly Tyr Leu Ala Val Ala Val Val Arg Arg Ser
    450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
    515                 520                 525

Gly Asp Glu Gln Gly Glu Asn Lys Cys Val Pro Asn Ser Asn Glu Arg
    530                 535                 540

Tyr Tyr Gly Tyr Thr Gly Ala Phe Arg Cys Leu Ala Glu Asn Ala Gly
545                 550                 555                 560

Asp Val Ala Phe Val Lys Asp Val Thr Val Leu Gln Asn Thr Asp Gly
                565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
            645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
    690                 695                 700

Ala Cys Glu Phe Leu Arg Lys
705                 710
```